United States Patent
Krumel et al.

(10) Patent No.: US 6,352,635 B2
(45) Date of Patent: Mar. 5, 2002

(54) SELECTIVE ELECTROCHEMICAL REDUCTION OF HALOGENATED 4-AMINOPICOLINIC ACIDS

(75) Inventors: Karl Leopold Krumel, Midland; Craig Joseph Bott, Clare; Michael Frederick Gullo, Midland; Carey Lee Scortichini, Midland; John Wesley Hull, Jr., Midland, all of MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/760,325

(22) Filed: Jan. 12, 2001

Related U.S. Application Data

(60) Provisional application No. 60/176,719, filed on Jan. 14, 2000.

(51) Int. Cl.$^7$ ................................................ C25B 3/00
(52) U.S. Cl. ................................................ 205/426
(58) Field of Search ................................................ 205/426

(56) References Cited

U.S. PATENT DOCUMENTS

| | | | | |
|---|---|---|---|---|
| 3,285,925 A | * | 11/1966 | Johnston et al. | 260/294.9 |
| 3,694,332 A | | 9/1972 | Parker et al. | 204/73 |
| 4,217,185 A | | 8/1980 | Kyriacou et al. | 204/73 |
| 4,242,183 A | | 12/1980 | Kyriacou | 204/73 |
| 6,297,197 B1 | * | 10/2001 | Fields et al. | 504/260 |

FOREIGN PATENT DOCUMENTS

RU 1807686 5/1994

* cited by examiner

*Primary Examiner*—Edna Wong
(74) *Attorney, Agent, or Firm*—Craig E. Mixan

(57) ABSTRACT

Halogen substituents in the 5-position of 4-aminopicolinic acids are selectively reduced in the presence of halogen substituents in the 3- and 6-positions by electrolysis.

12 Claims, No Drawings

SELECTIVE ELECTROCHEMICAL REDUCTION OF HALOGENATED 4-AMINOPICOLINIC ACIDS

This application claims the benefit of Provisional Application Ser. No. 60/176,719 filed Jan. 14, 2000.

BACKGROUND OF THE INVENTION

This invention concerns the preparation of certain 4-aminopicolinic acids by electrochemical reduction. More particularly, this invention concerns the selective reduction of halogen substituents in the 5-position of halogenated 4-aminopicolinic acids in the presence of halogen substituents in the 3- and 6-positions.

A co-pending U.S. Patent application filed concurrently with this application discloses certain 4-amino-3-halopicolinic acid derivatives and their use as herbicides. It would be desirable to be able to produce these herbicides in as few steps as possible from commercially available raw materials, such as 4-amino-3,5,6-trichloropicolinic acid (picloram).

While chemical reductions of halogenated pyridines are known, see, for example, U.S. Pat. No. 4,087,431 in which hydrazine is employed as a reducing agent, efficiency of material utilization is poor and costs are relatively high. Electrolytic reductions, on the other hand, can be very efficient as well as selective. U.S. Pat. No. 3,694,332 discloses the selective electrolytic reduction of halogenated pyridines and halogenated cyanopyridines in the 4-position. U.S. Pat. No. 4,217,185 discloses the electrolytic reduction of tetrachloropicolinic acid in the 4- and 5-positions. U.S. Pat. 4,242,183 discloses the electrolytic reduction of symmetrical tetrachloropyridine to 2,3,5-trichloropyridine using an activated silver mesh cathode. This patent also claims methods for activating the silver cathode. Russian Patent SU 1807686 A1 discloses the electrolytic reduction of polychlorinated pyridinecarboxylic acids. Such selective electrolytic reductions are limited to halogenated pyridines that contain only carboxylic acid or cyano substituents. It would be desirable to have electrochemical methods that could selectively reduce halogenated pyridines containing other substituents.

SUMMARY OF THE INVENTION

It has now been found according to the present invention that 4-amino-3-halopicolinic acids can be prepared by the electrochemical reduction of the corresponding 4-amino-3,5-dihalopicolinic acids. More particularly, the present invention concerns a process for the preparation of a 4-amino-3-halopicolinic acid of Formula I

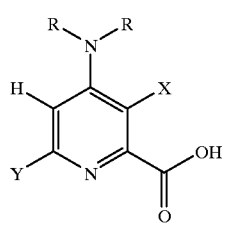

wherein
X represents Cl or Br;
Y represents H, F, Cl, Br or $C_1$–$C_4$ alkyl; and
R independently represents H or $C_1$–$C_4$ alkyl which comprises passing a direct or alternating electric current from an anode to a cathode through a solution of a 4-amino-3,5-dihalopicolinic acid of Formula II

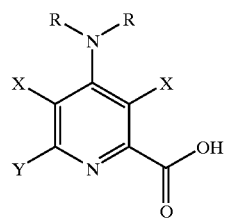

wherein
X, Y and R are as previously defined, and
wherein
both of X are either Cl or Br at a cathode potential of about −0.4 to about −1.7 volts relative to an Ag/AgCl (3.0 M Cl⁻) reference electrode and recovering the product, with the proviso that, when X is Cl, Y is not Br. Surprisingly, the halogen in the 5-position is selectively removed in the presence of the 4-amino group in high yield.

DETAILED DESCRIPTION OF THE INVENTION

The present invention concerns the selective electrochemical reduction of the 5-halo substituent of 4-amino-3,5-dihalopicolinic acids. As used herein, the term "halogen" or "halo" refers to Cl or Br.

The reactions involved in the reduction of the 4-amino-3,5-dihalopicolinic acid may be depicted as follows:
A) Neutralization:

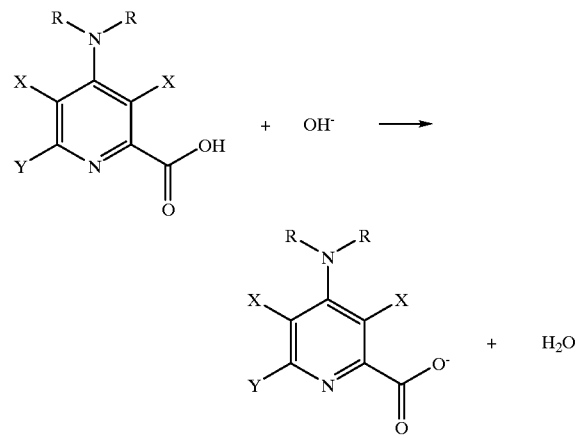

B) Cathode Reaction:

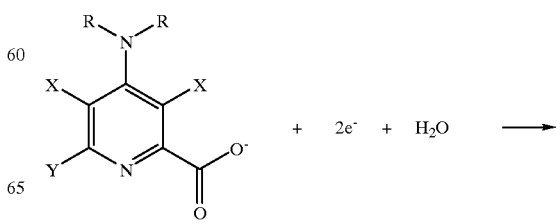

-continued

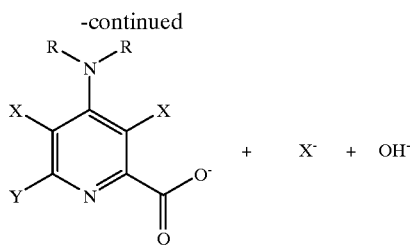

C) Anode Reaction:

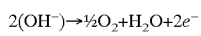

D) Overall Reaction:

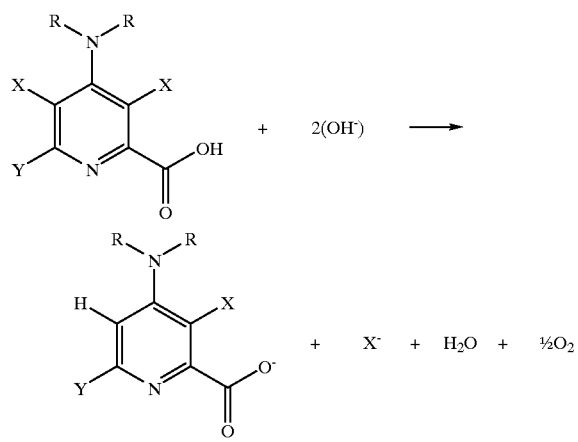

The carboxylic acid is recovered by acidifying the reaction mixture and recovering the product by conventional techniques.

The desired electrolytic reduction is carried out by techniques that are generally known in the art. In general, the starting 4-amino-3,5-dihalopicolinic acid is dissolved in a solvent to form an electrolyte which is added to the electrolytic cell while enough current is passed through the electrolyte until the desired degree of reduction is obtained.

It should be appreciated by those skilled in the art that the reduction potential of bromine is about 0.5 volt higher (less negative) than the comparable chlorine potential. The bromine will always be reduced off first. Thus, when X is Cl, Y cannot be Br.

The design of the electrolysis cell is not critical. The electrolysis can be conducted batch-wise, or in a continuous or semi-continuous fashion. The cell may be a stirred tank containing the electrodes or a flow cell of any conventional design. In some cases, it may be desirable to employ a separator to divide the cell into separate anodic and cathodic compartments. Examples of useful separator materials are various anion and cation exchange membranes, porous Teflon, asbestos, and glass. While the use of three electrodes in which the potential of the cathode is controlled relative to a reference electrode is preferred, the electrolysis can alternatively be performed using only two electrodes, an anode and a cathode, and controlling either the cell current, the cell voltage, or both. For convenience, a 3-electrode undivided cell in which the electrolyte serves as both the catholyte and the anolyte is preferred.

The anode can be any chemically inert material including, for example, platinum, graphite, carbon, metal oxides such as silver oxide on silver, or alloys such as Hastelloy C, with graphite, carbon and Hastelloy C being preferred. Similarly the cathode can be constructed from a number of materials, including mercury, lead, iron, tin, zinc or silver, with silver being preferred. Electrodes may be in the form of plates, rods, wires, screens, gauze, wool, sheets or pools, with expanded mesh screens being preferred. The anode or cathode may also consist of a coating applied to another material, an example of which is a noble metal oxide such as ruthenium oxide coated onto titanium.

The most preferred cathodes are activated silver cathodes prepared as described in U.S. Pat. Nos. 4,217,185 and 4,242,183. Such activated cathodes can be prepared by depositing a layer of silver microcrystals on a conductive substrate to form a composite electrode or by anodization of a silver electrode itself. For example, to illustrate the latter, an unactivated silver electrode can be dipped or immersed in an aqueous caustic catholyte solution and anodized, thus converting some of the silver at the surface of the electrode to colloidal silver oxide and roughening the surface at the same time. The polarity of the electrode is then reversed and the oxide electrolytically converted into particles of microcrystalline silver adhered to the surface of the electrode. The activation procedure involves increasing the potential from an initial value of zero volts to a final value of at least +0.3 volts and preferably about +0.7 volts. Reduction of the oxide deposit requires negative polarization of the cathode. The cathode potential is gradually reduced from the value of about +0.3 to about +0.7 volts attained during the oxidation step, to a value of about −0.5 volts or less. It is not necessary to add any silver to the catholyte or aqueous base in this method.

Water is the most preferred solvent for the electrolysis but, in some circumstances, it is possible to use an organic solvent either alone or as a co-solvent. The solvent or the co-solvent system should dissolve all or most of the starting material and the electrolyte, or at least enough to allow the reduction to proceed at a reasonable rate. In addition, the solvent or the co-solvent system should be inert to the electrolysis conditions, i.e., it does not detrimentally alter or react with the cathode or the catholyte materials to an intolerable extent. Other than water, preferred solvents/co-solvents are miscible with water and include lower molecular weight alcohols, ethers such as tetrahydrofuran, dioxane and polyglycol ethers, and lower amides such as dimethyl formamide or dimethyl acetamide.

Alkali metal hydroxides are preferred as the supporting electrolyte but many other substances such as quaternary ammonium or metallic hydroxides, chlorides, carbonates, etc. may be used. NaOH is the most preferred supporting electrolyte.

In the reaction, one equivalent of base is required to neutralize the starting material and an additional equivalent is required to generate hydroxyl ions that are consumed in the electrolysis. The reaction is typically run with an excess of base, preferably with a 0.05 to 2 weight percent excess of base throughout the reaction.

The concentration of halogenated 4-aminopicolinic acid in the catholyte or feed can be from about 1 to about 20 percent by weight, preferably from about 8 to about 12 percent by weight. Lower concentrations reduce productivity while higher concentrations usually result in lower yields, lower product purity and lower electrical efficiencies.

Suitable temperatures for the electrolysis generally range from about 5 to about 90° C. The preferred temperature range is from about 20 to about 60° C. From about 20 to about 40° C. is most preferred.

One skilled in the art will appreciate that the apparent cathode potential at which the halogen will be selectively reduced, is dependent on a variety of factors including, for example, the structure of the particular substrate, the cell configuration, and the distance separating the electrodes. In general, the cathode potential, relative to a standard Ag/AgCl (3.0 M Cl$^-$) electrode, should be within the range of about −0.4 to about −1.1 volts for Br and within the range of about −0.8 to about −1.7 volts for Cl. For Br, the cathode potential is preferably from about −0.6 to about −0.9 volts. For Cl, the cathode potential is preferably from about −1.0 to about −1.4 volts. The current density in amperes per square centimeter (amp/cm$^2$) should be at least 0.005, preferably about 0.05 amp/cm$^2$ or greater.

While the evolution of molecular oxygen is preferred, many other anodic reactions can be employed. Examples include the evolution of molecular chlorine or bromine, oxidation of a sacrificial species such as formate or oxalate to give carbon dioxide, or the oxidation of an organic substrate to form a valuable co-product.

In the presently preferred mode of operation, a halogenated 4-aminopicolinic acid is dissolved in aqueous caustic to form a basic aqueous solution which is continuously recirculated through an undivided electrochemical cell having an expanded silver mesh cathode activated by anodization at +0.7 volts in an aqueous caustic electrolyte. While keeping the reaction mixture alkaline, electrolysis at a cathode potential of from about −0.6 to about −1.5 volts relative to an Ag/AgCl (3.0 M Cl$^-$) reference electrode is continued until the desired degree of reduction has occurred. The desired product is recovered by conventional techniques. For example, the acid can be precipitated from the reaction mixture by acidification followed by either filtration or extraction with a water immiscible organic solvent.

The following examples are illustrative of the present invention.

EXAMPLE

Example 1

Preparation of 4-amino-3,6-dichloropyridine-2-carboxylic acid (Flow Through Cell)

In a 3-liter (L) beaker was added 2000 grams (g) of hot water, 115.1 g of 50 percent by weight NaOH, and 200 g of wet 4-amino-3,5,6-trichloropyridine-2-carboxylic acid (79.4 percent). The solution was stirred for 30 minutes (min), filtered through a paper filter, and transferred to a 5-L feed/recirculation tank. This solution weighed 2315 g and contained 6.8 percent 4-amino-3,5,6-trichloropyridine-2-carboxylic acid. This feed was recirculated at a rate of about 9.46 L/min and a temperature of 30° C. through an undivided electrochemical cell having a Hastelloy C anode (15 cm×4 cm) and an expanded silver mesh cathode (15 cm ×4 cm). After normal anodization at +0.7 volts (v), the polarity of the cell was reversed and the electrolysis was started. The cathode working potential was controlled at −1.1 to −1.4 v relative to an Ag/AgCl (3.0 M Cl$^-$) reference electrode. The reference electrode was physically located directly behind the silver cathode and connected electrically with an aqueous salt bridge. While recirculating the feed, a solution of 50 percent NaOH was slowly pumped into the recirculation tank to maintain the NaOH concentration at a 1.5 to 2.0 percent excess. The current ranged from 1.0 to 5.2 amps.

After about 15 hours (h) and about 213,100 coulombs had been passed through the system, the electrolysis was terminated and the cell effluent was filtered through a paper filter. The solution was neutralized with concentrated HCl and concentrated to about 750 g of crude concentrate. The concentrate was warmed to 85° C. while stirring and the pH was adjusted to less than 1 with concentrated HCl over 30 min. The resulting slurry was cooled to ambient temperature and filtered. The filter cake was washed with 3×200 milliliter (mL) portions of water and dried under vacuum at 80° C. The dried product, 118.1 g assayed at 90.6 percent desired product; gas chromatography (GC) indicated about 4 percent 4-amino-3,5,6-trichloropyridine-2-carboxylic acid remaining as an impurity. A purified sample of 4-amino-3,6-dichloropyridine-2-carboxylic acid had a melting point (mp) of 185–187° C. (dec.); $^1$H NMR (DMSO-d$_6$): δ13.9 (br, 1H), 7.0 (br m, 2H), 6.8 (s,1H); $^{13}$C NMR {$^1$H} (DMSO-d$_6$): δ165.4 (1C), 153.4 (1C), 149.5 (1C), 147.7 (1C), 111.0 (1C), 108.1 (1C).

Example 2

Preparation of 4-amino-3,6-dichloropyridine-2-carboxylic acid (Batch Cell)

The cell was a 180 mL beaker (2 in. (5.1 cm) diameter× 4.5 in. (11.4 cm) tall). The silver mesh cathode consisted of a 1 in. (2.5 cm)×4 in. (10.2 cm) strip placed around the inside wall of the beaker approximately 0.5 in. (1.3 cm) off the bottom and had a 0.5 in. (1.3 cm) wide strip extending out the top of the beaker to which the power supply was attached. The anode was a 0.75 in. (1.9 cm) diameter×6 in. (15.2 cm) long graphite rod that was supported by a rubber stopper in the middle of the beaker and extended to about 0.5 in. (1.3 cm) off the bottom. The working potential of the cathode was controlled relative to an Ag/AgCl (3.0 M Cl$^-$) reference electrode positioned between the silver mesh and the wall of the beaker.

The silver mesh cathode was activated by anodization at +0.7 volt (v) in a 2% sodium hydroxide and 1% sodium chloride solution in water followed by reverse polarization. After activation, the solution was replaced with a solution of 81 mL of water, 5.1 g (0.0213 moles) of 4-amino-3,5,6-trichloropicolinic acid, and 2.8 g (0.0426 moles) of 85% KOH. After sparging with a slow stream of nitrogen, the electrolysis was carried out at a working potential of −1.3 to −1.35 volts for 2 hours at ambient temperature. The current started at 0.83 amps and gradually decreased to 0.25 amps after the two hours. A total of 5000 coulombs were passed through the solution (theory for reduction of one chlorine off the pyridine ring is 2050 coulombs). Analysis of the crude product solution by gradient elution HPLC showed the disappearance of the starting material and the appearance of a single peak later identified as 4-amino-3,6-dichloropicolinic acid.

Example 3

Preparation of 4-amino-3,6-dibromopyridine-2-carboxylic acid (Batch Cell)

The same batch electrolysis cell as described in Example 2 was used.

The cell was charged with 75 mL of a solution of 1% sodium chloride and 2% sodium hydroxide in water. The silver cathode was activated and then 0.635 g of 4-amino-3,5,6-tribromopicolinic acid methyl ester was added to the solution in the cell. After warming the solution to about 75° C. for 30 minutes to hydrolyze the ester to the carboxylate anion, the solution was cooled to room temperature. The electrolysis was performed during 45 minutes at a cathode working potential of −0.7 volts. The current ranging from 0.44 amps at the start and dropped to 0.12 amps at the end of the reaction. A total of 400 coulombs were passed.

The electrolysis solution was recovered, the pH of the solution was adjusted to neutral and the solution was evaporated to dryness. The recovered solids were dissolved in acetonitrile-water mixture and the product was recovered by preparative HPLC. A sample of 110 mg of a single isomer, purity >98% by HPLC and 1H NMR, identified as 4-amino-3,6-dibromopicolinic acid, was obtained.

What is claimed is:

1. A process for the preparation of a 4-amino-3-halopicolinic acid of Formula I

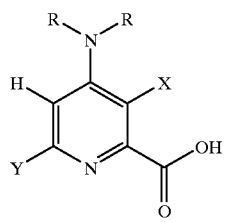

I wherein
X represents Cl or Br;
Y represents H, F, Cl, Br or $C_1$–$C_4$ alkyl; and
R independently represents H or $C_1$–$C_4$ alkyl
which comprises passing a direct or alternating electric current from an anode to a cathode through a solution of a 4-amino-3,5-dihalopicolinic acid of Formula II

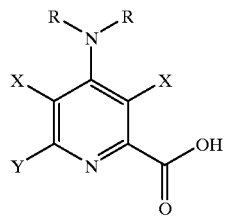

II wherein
X, Y and R are as previously defined, and wherein
both of X are either Cl or Br at a cathode potential of about −0.4 to about −1.7 volts relative to an Ag/AgCl (3.0 M Cl⁻) reference electrode and recovering the product, with the proviso that, when X is Cl, Y is not Br.

2. The process of claim 1 in which the compound of Formula II is

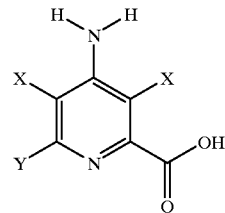

wherein X and Y are as previously defined.

3. The process of claim 1 in which the solution of the 4-amino-3,5-dihalopicolinic acid is a basic aqueous solution.

4. The process of claim 1 in which X is Cl and the cathode potential is from about −0.8 to about −1.7 volts.

5. The process of claim 4 in which Y is Cl.

6. The process of claim 5 in which the cathode potential is from about −1.0 to about −1.4 volts.

7. The process of claim 1 in which X is Br and the cathode potential is from about −0.4 to about −1.1 volts.

8. The process of claim 7 in which Y is Br.

9. The process of claim 8 in which the cathode potential is from about −0.6 to about −0.9 volts.

10. The process of claim 1 in which the cathode is silver.

11. The process of claim 10 in which the silver cathode has been activated by anodization in an aqueous caustic solution at a potential of at least +0.3 to about +0.7 volts followed by reverse polarization.

12. A process for the preparation of

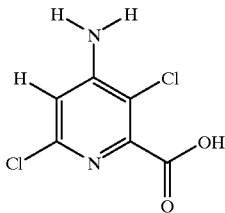

which comprises passing a direct or alternating electric current from an anode to a silver cathode through a basic aqueous solution of

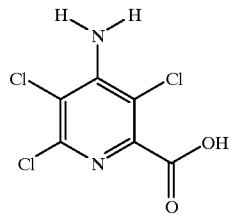

at a cathode potential of about −1.0 to about −1.4 volts relative to an Ag/AgCl (3.0 M Cl⁻) reference electrode, acidifying the reaction mixture and recovering the product.

* * * * *